United States Patent
Asafusa

(12) 
(10) Patent No.: US 6,299,580 B1
(45) Date of Patent: *Oct. 9, 2001

(54) ULTRASONIC PROBE AND ULTRASONIC DIAGNOSTIC APPARATUS USING THE SAME

(75) Inventor: Katsunori Asafusa, Matsudo (JP)

(73) Assignee: Hitachi Medical Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/308,381

(22) PCT Filed: Jun. 17, 1998

(86) PCT No.: PCT/JP97/04218

§ 371 Date: May 18, 1999

§ 102(e) Date: May 18, 1999

(30) Foreign Application Priority Data

Nov. 19, 1996 (JP) .................................................. 8-307627

(51) Int. Cl.[7] ....................................................... A61B 8/00
(52) U.S. Cl. ............................................................. 600/459
(58) Field of Search .................................. 600/459, 462, 600/472, 440, 443

(56) References Cited

U.S. PATENT DOCUMENTS

| | | | |
|---|---|---|---|
| 4,281,550 | * 8/1981 | Erikson | 600/472 |
| 5,042,493 | * 8/1991 | Saito et al. | 600/459 |
| 5,164,920 | * 11/1992 | Bast et al. | 600/459 |
| 5,417,219 | * 5/1995 | Takamizawa et al. | 600/472 |
| 5,848,969 | * 12/1998 | Pangscu et al. | 600/462 |

* cited by examiner

*Primary Examiner*—William E. Kamm
(74) *Attorney, Agent, or Firm*—Antonelli, Terry, Stout & Kraus, LLP

(57) ABSTRACT

An ultrasonic probe which improves the directivity of the ultrasonic transmission beam by reducing the grating lobes at the time of transmitting ultrasonic waves. An ultrasonic probe 1 comprising a plurality of transducers 2 for transmitting ultrasonic waves and for receiving the reflected echoes thereof, and having a backing member 3 formed on the back surfaces of said transducers 2 as well as an acoustic matching layer and an acoustic lens formed on the front surfaces of said transducers, wherein the transducers 2 are formed in the shape of a predetermined small block and are arranged in many number in a spherical shape on the front surface of the backing member 3 formed in a spherical surface protruding in a semicircular manner. By applying the transmission signals which are in phase to the number of the transducers 2 to drive them, the sound pressure of the transmitted ultrasonic waves uniformly propagate in all directions, establishing a transmission from a point source of sound. By reducing the grating lobes at the time of transmitting ultrasonic waves, furthermore, the directivity of the ultrasonic transmission beam is improved.

14 Claims, 6 Drawing Sheets

(a)

(b)

(a)

(b)

ULTRASONIC PROBE AND ULTRASONIC DIAGNOSTIC APPARATUS USING THE SAME

TECHNICAL FIELD

The present invention relates to an ultrasonic probe which enables the improvement of directivity of an ultrasonic transmission beam by reducing the grating lobes at the time of transmitting ultrasonic waves, and to an ultrasonic diagnostic apparatus using the ultrasonic probe as a probe for transmitting and receiving ultrasonic waves to and from a diagnosing part of a subject.

BACKGROUND ART

A conventional ultrasonic probe comprises a plurality of transducers that transmit ultrasonic waves and receive reflected echoes thereof, a backing member provided on the back surfaces of the transducers so that ultrasonic waves transmitted from the transducers will not return back again, an acoustic matching layer formed on the front surfaces of the transducers to match the difference between the acoustic impedance of the transducers and the acoustic impedance of the living body, and an acoustic lens provided on the upper surface of the acoustic matching layer to converge the ultrasonic beam. The plurality of transducers are formed in the shape of short strips which are linearly arranged in a one-dimensional manner, or in a two-dimensional manner, or are so arranged in many number that the ultrasonic wave transmitting/receiving surfaces are formed in an arcuate shape, thereby to constitute an ultrasonic probe.

The scanning of the ultrasonic beam by the above-mentioned ultrasonic probe is effected in combination of an ultrasonic transmission beam and an ultrasonic reception beam by driving the ultrasonic probe. That is, transmission signals that are time delayed are added to the transducers, to form an ultrasonic transmission beam that converges the ultrasonic waves at a given point, and the reflected echo signals received by the transducers are delayed to effect the phasing thereby to form an ultrasonic reception beam. Furthermore, an ultrasonic beam in the direction of short axis of the transducers arranged in many number is converged through an acoustic lens or the like to control the slicing thickness of the tomographic image. Moreover, two to four ultrasonic reception beams are used in combination for an ultrasonic transmission beam of one direction, to increase the number of scanning lines of the ultrasonic beams, thereby attempting to shorten the scanning time and to improve the resolution of the ultrasonic image. In order to obtain a three-dimensional image, furthermore, the two-dimensional scanning of the ultrasonic beam is effected a plural number of times in the slicing direction with respect to the subject.

By using the conventional ultrasonic probe, however, the ultrasonic transmission beam exhibits directivity. Besides, with the transducers of the conventional shape and arrangement, ultrasonic waves called grating lobes are generated in the transverse direction in addition to main lobes. Therefore, the directivity of the ultrasonic transmission beam is often deteriorated. The presence of the grating lobes causes a difference in the sensitivity among the ultrasonic beams when the number of the ultrasonic beams is increased by using a plurality of ultrasonic reception beams. Due to the difference in the sensitivity, therefore, limitation is imposed on the number of the ultrasonic reception beams and, hence, limitation is imposed on accomplishing a high frame rate of the obtained ultrasonic image. In obtaining a three-dimensional diagnostic image by using the conventional ultrasonic probe, furthermore, it is not often allowed to three-dimensionally diagnose the moving portion of the subject due to limitation on the number of the ultrasonic beams and limitation on increasing the frame rate.

In order to cope with the above-mentioned problems, therefore, the object of the present invention is to provide an ultrasonic probe which enables the improvement of directivity of an ultrasonic transmission beam by reducing the grating lobes at the time of transmitting ultrasonic waves, and an ultrasonic diagnostic apparatus using the ultrasonic probe as a probe for transmitting and receiving ultrasonic waves to and from a diagnosing part of a subject.

DISCLOSURE OF THE INVENTION

In order to accomplish the above-mentioned object, an ultrasonic probe according to the present invention comprises a plurality of transducers for transmitting ultrasonic waves and for receiving the reflected echoes thereof, and has a backing member formed on the back surfaces of the transducers as well as an acoustic matching layer and an acoustic lens formed on the front surfaces of the transducers, wherein the transducers are arranged in a spherical shape.

Further, with the present invention, there is provided an ultrasonic probe comprising a plurality of transducers for transmitting ultrasonic waves and for receiving the reflected echoes thereof, and having a backing member formed on the back surfaces of the transducers as well as an acoustic matching layer and an acoustic lens formed on the front surfaces of the transducers, wherein the transducers are formed in the shape of a predetermined small block, and the number of the transducers in the form of a small block are arranged in a spherical shape on the front surface of the backing member formed in the shape of a spherical surface protruding in a semispherical manner.

The transducers may be formed in the shape of a circular plate or a polygonal plate, and the transducers of the shape of the circular plate only or the transducers of the shape of the polygonal plate only, or the transducers of the shape of the circular plate and the transducers of the shape of the polygonal plate in combination, may arranged in a spherical shape.

Furthermore, the invention is concerned with an ultrasonic diagnostic apparatus as a related invention comprises a probe having a plurality of transducers that are arranged to transmit and receive ultrasonic waves into, and from, a subject, a transmission unit for transmitting transmission signals to the transducers in the probe to transmit ultrasonic waves, a reception unit for amplifying, phasing and adding the reflected echo signals from said probe, a signal processing unit for processing reception signals from the reception unit, an image storage unit for storing image data by converting the reception signals after processed into image data and effecting the image processing, a display unit for displaying the image data from the image storage unit, a control unit for controlling the operations of said constituent elements, and an input device for inputting operation instructions to said control unit, wherein the ultrasonic probe mentioned above is used as said probe, transmission signals which are in phase are sent from said transmission unit to the number of the transducers constituting the probe to generate a sound field equivalent to the one generated by a point source of sound without directivity, and said reception unit simultaneously generates a plurality of reception beams upon receiving the reception signals from the probe.

The image storage unit may have a frame memory that stores the image data for simultaneously displaying at least two or more two-dimensional tomographic images or the image data for displaying a three-dimensional image.

BEST MODE FOR CARRYING OUT THE INVENTION

Embodiments of the present invention will now be described in detail with reference to the accompanying drawings.

Figure 1:
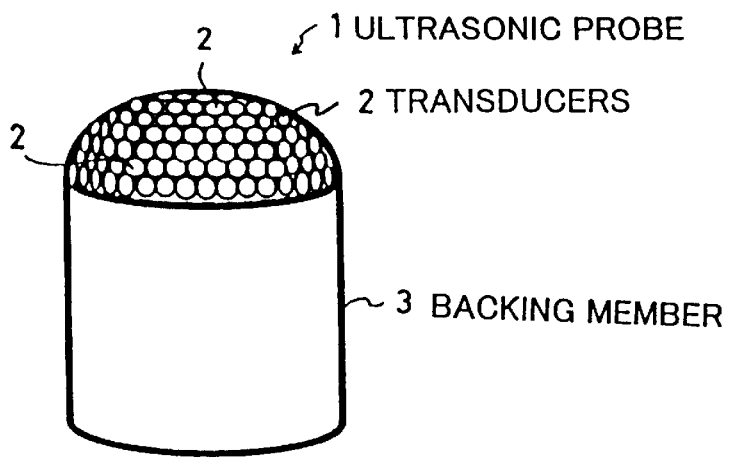
FIG. 1 is a perspective view illustrating an embodiment of an ultrasonic probe according to the present invention.

FIG. 1 is a perspective view illustrating an embodiment of an ultrasonic probe according to an embodiment of the present invention. An ultrasonic probe 1 works as a measuring unit for transmitting and receiving ultrasonic waves into, and from, a subject, and is used in an ultrasonic diagnostic apparatus which obtains an ultrasonic image of a diagnosing part of the subject by utilizing ultrasonic waves. As shown in FIG. 1, the ultrasonic probe 1 comprises a plurality of transducers 2, 2, - - - for transmitting ultrasonic waves and for receiving reflected echoes thereof, and has a backing member 3 formed on the back surfaces of the transducers 2 and an acoustic matching layer (not shown) formed on the front surfaces thereof.

The plurality of transducers 2 transmit ultrasonic waves and receive reflected echoes thereof, and are made up of piezo-electric elements of such a material as ZnO or PZT. Electrodes are formed on both surfaces of the piezo-electric elements, and a voltage is applied across the electrodes, so that the piezo-electric elements are expanded and contracted in the direction of the thickness. The backing member 3 is formed on the back surfaces of the transducers 2 and so works that the ultrasonic waves transmitted from the transducers 2 will not return back again. The backing member 3 is made of a material which greatly attenuates the ultrasonic waves. Furthermore, though not diagramed, the acoustic matching layer is formed on the front surfaces of the transducers 2, and works to match the difference between the acoustic impedance of the transducers 2 and the acoustic impedance of a living body. The acoustic matching layer is made of a material having an acoustic impedance that lies between those of the transducers and the living body.

Figure 2:
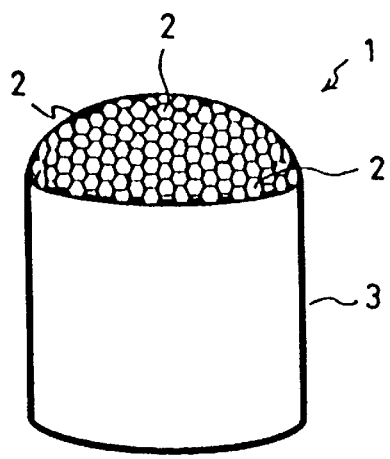
FIG. 2 is a perspective view illustrating another embodiment of the ultrasonic probe according to the present invention.

Here, according to the present invention, the transducers 2 are formed in the shape of a predetermined small block, and the number of the transducers 2, 2, - - - in the form of a small block are arranged in a spherical shape on the front surface of the backing member 3 which is formed in a spherical surface protruding in a semispherical manner. That is, as shown in FIG. 1, the transducers 2 are formed in the shape of a circular plate having a diameter of from several microns to several millimeters. Or, as shown in FIG. 2, the transducers 2 are formed in the shape of a polygonal plate such as a hexagonal plate having a side of from several microns to several millimeters. The transducers are prepared by, for example, forming a thin film by sputtering followed by cutting. As shown in FIGS. 1 and 2, furthermore, the front surface of the backing member 3 is formed in a spherical surface protruding in a semispherical manner. The number of the transducers 2, 2, - - - as mentioned above are arranged in a spherical shape on the front surface of the backing member 3 that is formed in a shape as described above. The transducers can be arranged by, for example, mounting them by using an automatic chip-mounting machine and applying wire boding to their terminals on the side of the backing member 3.

In FIG. 1, the transducers 2 of the shape of a circular plate only were arranged in many number in a spherical shape and in FIG. 2, the transducers 2 of the shape of a polygonal plate only were arranged in many number in a spherical shape. Not being limited thereto only, however, it is also allowable to arrange the transducers 2 of the shape of a circular plate and the transducers 2 of the shape of a polygonal shape alternately and in a spherical shape as a whole.

Figure 3:
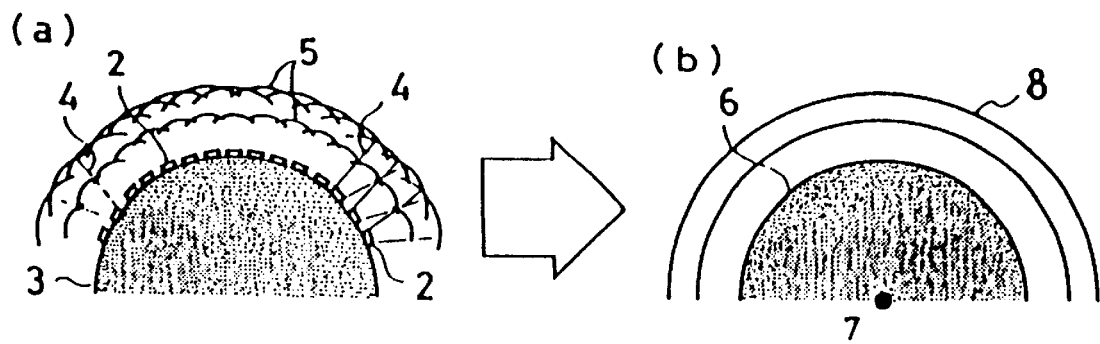
FIG. 3 is a diagram illustrating a manner of propagation of ultrasonic waves using the above-mentioned ultrasonic probe.

As described above, the number of the transducers 2, 2, - - - are arranged in a spherical shape. Upon sending transmission signals which are in phase from the ultrasonic diagnostic apparatus that is not shown to the number of the transducers 2, 2, - - - mentioned above, ultrasonic waves 4, 4, - - - having particular directivities are transmitted from the respective transducers 2, 2, - - - as shown in FIG. 3, part (a). In this case, the ultrasonic waves 4, 4, - - - are radially transmitted from the transducers 2, 2, - - - . Here, if attention is given to the crest and trough of the sound pressure of the ultrasonic waves 4 at that time, the wave fronts 5 propagate successively describing concentric circles with the center of a sphere on which the transducers 2, 2, - - - are arranged as a center. This is equivalent to a state where a point source of sound 7 is present at the center of a spherical surface 6 on which the transducers 2, 2, - - - are arranged as shown in FIG. 3, part (b), and ultrasonic waves 8 are uniformly transmitted from the point source of sound 7.

Figure 4:
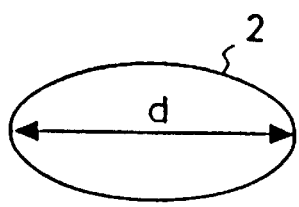
FIG. 4 is a diagram illustrating the directivity of an ultrasonic transmission beam by using transducers of the shape of a circular plate.
Figure 4:
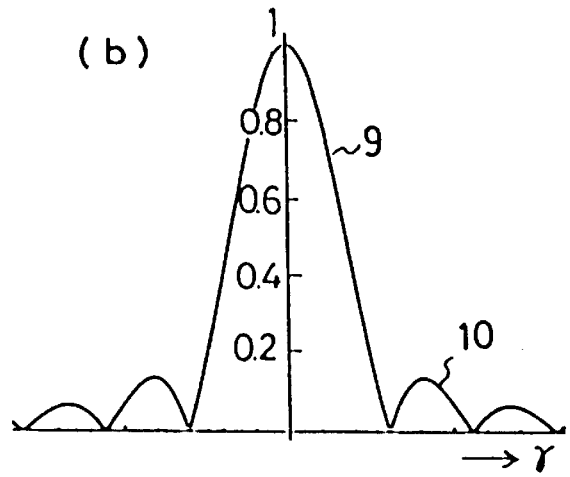
Figure 5:
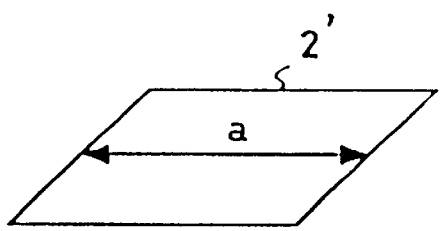
FIG. 5 is a diagram illustrating the directivity of an ultrasonic transmission beam by using transducers of the shape of a square plate.
Figure 5:
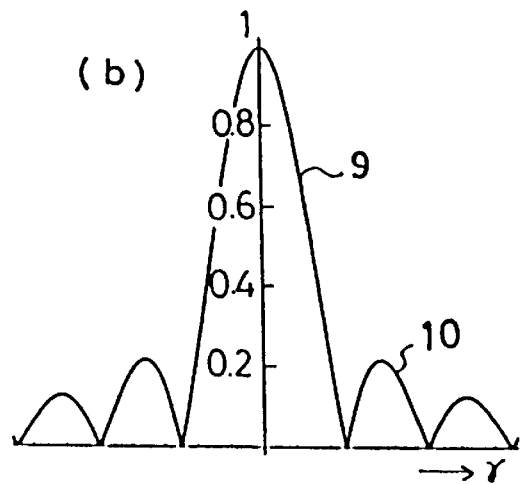

In practice, however, the ultrasonic wave transmission beam from the transducer 2 has a directivity as described above. FIGS. 4 and 5 illustrate how the directivity changes depending upon the shape of the transducer 2. FIG. 4 illustrates the directivity of when the transducer 2 is of the shape of a circular plate. Here, as shown in FIG. 4, part (a), if the diameter of the transducer 2 of the shape of a circular plate is denoted by d, the wavelength of the ultrasonic waves that are transmitted is denoted by $\lambda$ and the azimuth angle from the center of the main lobe 9 is denoted by $\gamma$ in FIG. 4, part (b), then, a factor Z of the Bessel function J1(Z) is expressed by the following formula (1), and a directivity function R that represents the height of the main lobe 9 in FIG. 4, part (b) is expressed by the following formula (2), $$Z = (\pi d/\lambda) \sin \gamma \qquad (1)$$

$$R = 2J1(Z)/Z \qquad (2)$$

FIG. 5 illustrates the directivity of when the transducer 2' has the shape of a polygonal plate. Here, as shown in FIG. 5, part (a), if the length of a side of the transducer 2' of the shape of a square plate is denoted by a, the wavelength of the ultrasonic waves that are transmitted is denoted by $\lambda$ and the azimuth angle from the center of the main lobe 9 is denoted by $\gamma$ in FIG. 5, part (b), then, a factor Z of the Bessel function J1(Z) is expressed by the following formula (3), and a directivity function R that represents the height of the main lobe 9 in FIG. 5, part (b) is expressed by the following formula (4), $$Z=(2\pi a/\lambda)\sin \gamma \qquad (3)$$

$$R=(\sin Z)/Z \qquad (4)$$

Here, if the directivity of the transducer 2 of the shape of a circular plate of FIG. 4 is compared with the directivity of the transducer 2' of the shape of a square plate of FIG. 5, the following can be said. That is, in the case of the transducer 2 of the shape of a circular plate shown in FIG. 4, part (b), the width of the main lobe 9 increases but the level of the grating lobes 10 decreases compared with those of the case of the transducer 2' of the shape of a square plate shown in FIG. 5, part (b). It will therefore be understood that the transducer 2 of the shape of a circular plate gives more improved directivity than the transducer 2' of the shape of a square plate. It can be generally said that the directivity increases with an increase in the number of corners of a polygon. Furthermore, the directivity can be improved by decreasing the gap among the transducers 2, decreasing the diameter of the transducers, and increasing the number of the transducers. Upon driving the ultrasonic probe 1 of the present invention by applying transmission signals thereto, therefore, the sound pressure of the transmitted ultrasonic waves uniformly propagates in all directions establishing a transmission from a point source of sound. By decreasing the gap for arranging the transducers 2, furthermore, the main lobes uniformly propagate in all directions being overlapped one upon the other establishing a transmission from a point source of sound.

By employing the transducers 2 of the shape of a circular plate or of a polygonal shape and arranging them at an equal interval, furthermore, the data related to the amount of delay in one direction can be used in common with the data related to the amount of delay in the other direction in forming an ultrasonic reception beam in the ultrasonic diagnostic apparatus to be described later. This makes it possible to decrease the number of data, to decrease the amount of operation, to reduce the scale of the circuit of the apparatus, to carry out the processing at an increased speed, and to accomplish a high frame rate.

Figure 6:
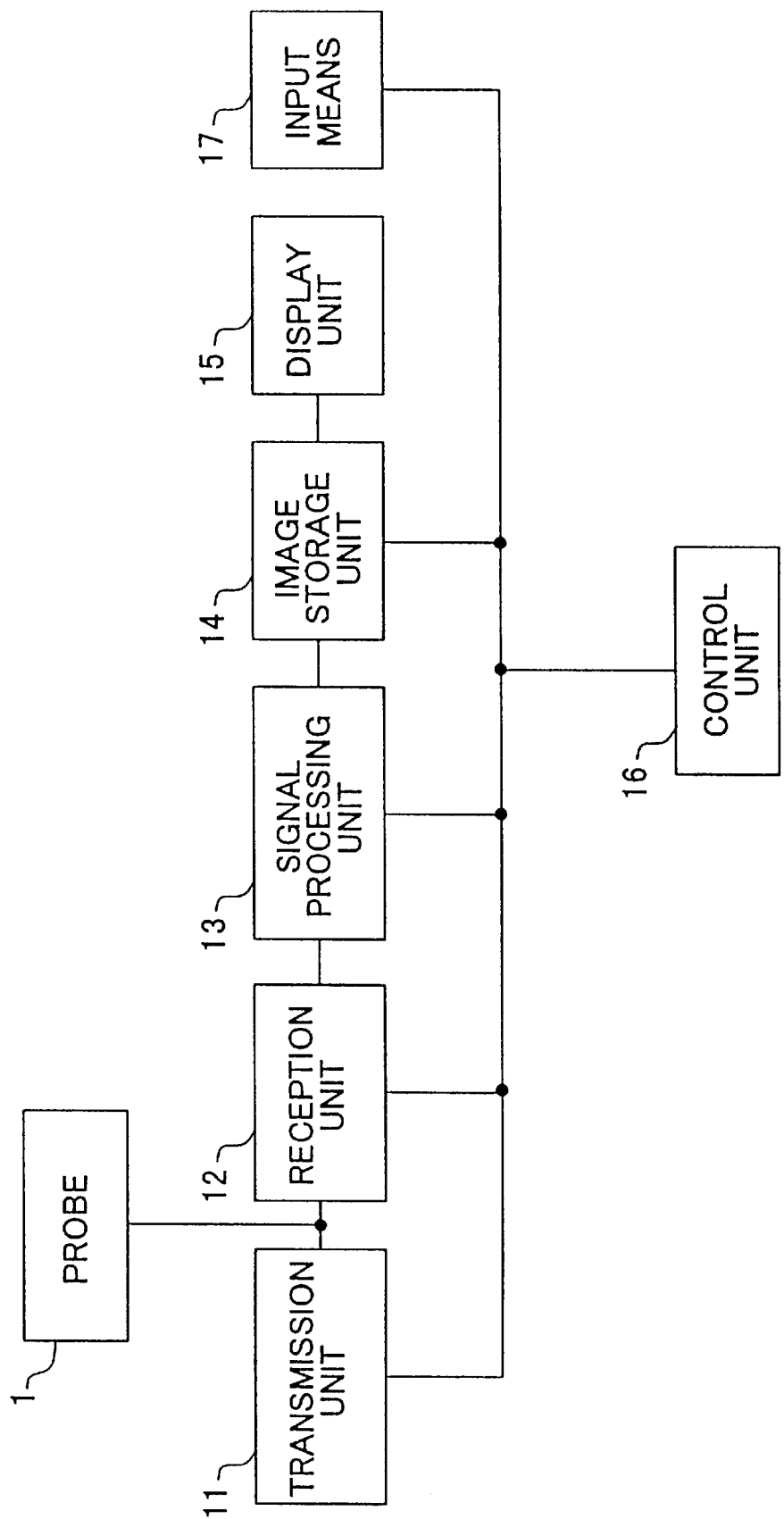
FIG. 6 is a block diagram illustrating an ultrasonic diagnostic apparatus according to an invention related to the above-mentioned ultrasonic probe.

FIG. 6 is a block diagram illustrating an ultrasonic diagnostic apparatus according to an invention related to the above-mentioned ultrasonic probe. The ultrasonic diagnostic apparatus collects and displays a tomographic image at the diagnosing part of a subject by utilizing the ultrasonic waves, and comprises, as shown in FIG. 6, a probe 1, a transmission unit 11, a reception unit 12, a signal processing unit 13, an image storage unit 14, a display unit 15, a control unit 16, and an input device 17.

Figure 7:
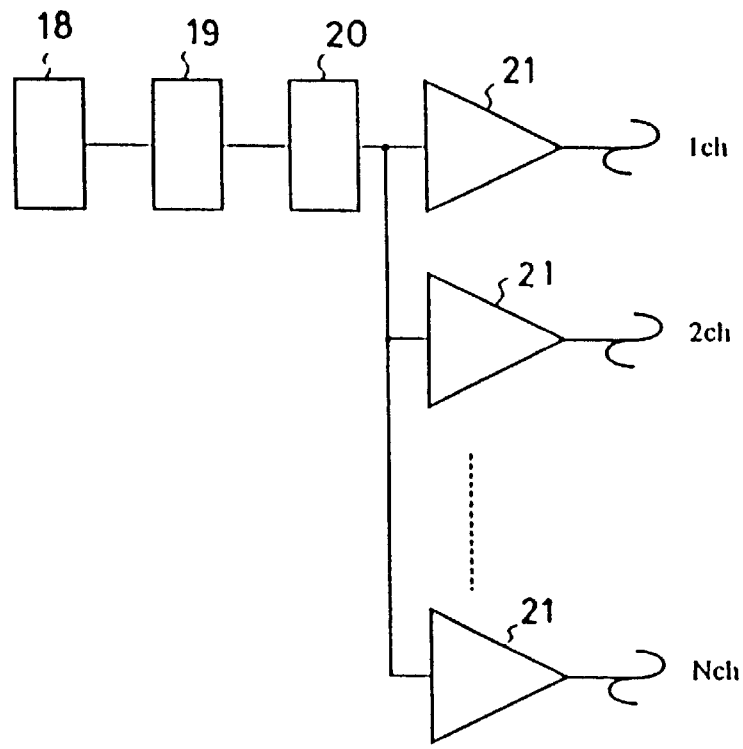
FIG. 7 is a block diagram illustrating the internal constitution of a transmission unit.
Figure 8:
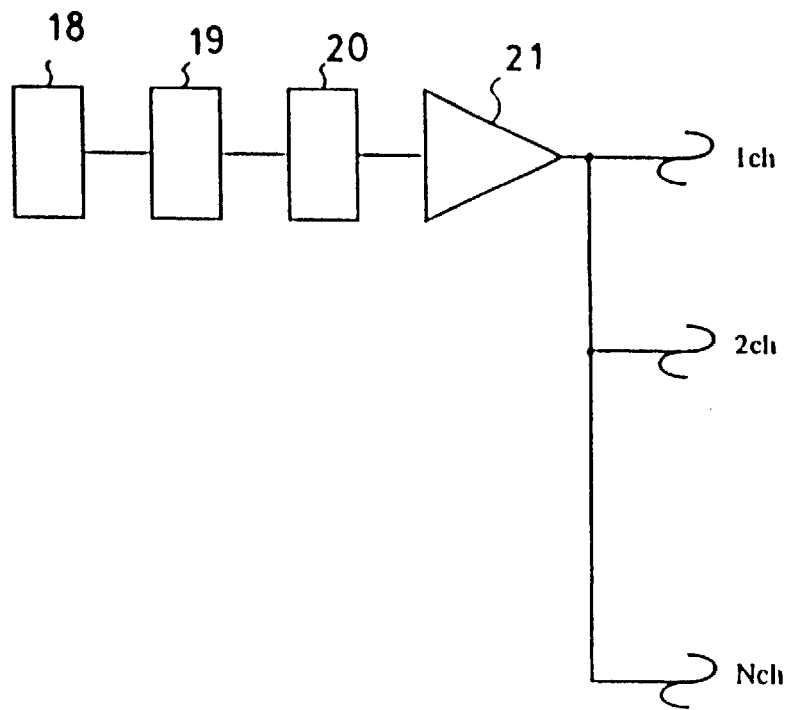
FIG. 8 is a block diagram illustrating another internal constitution of the transmission unit.
Figure 9:
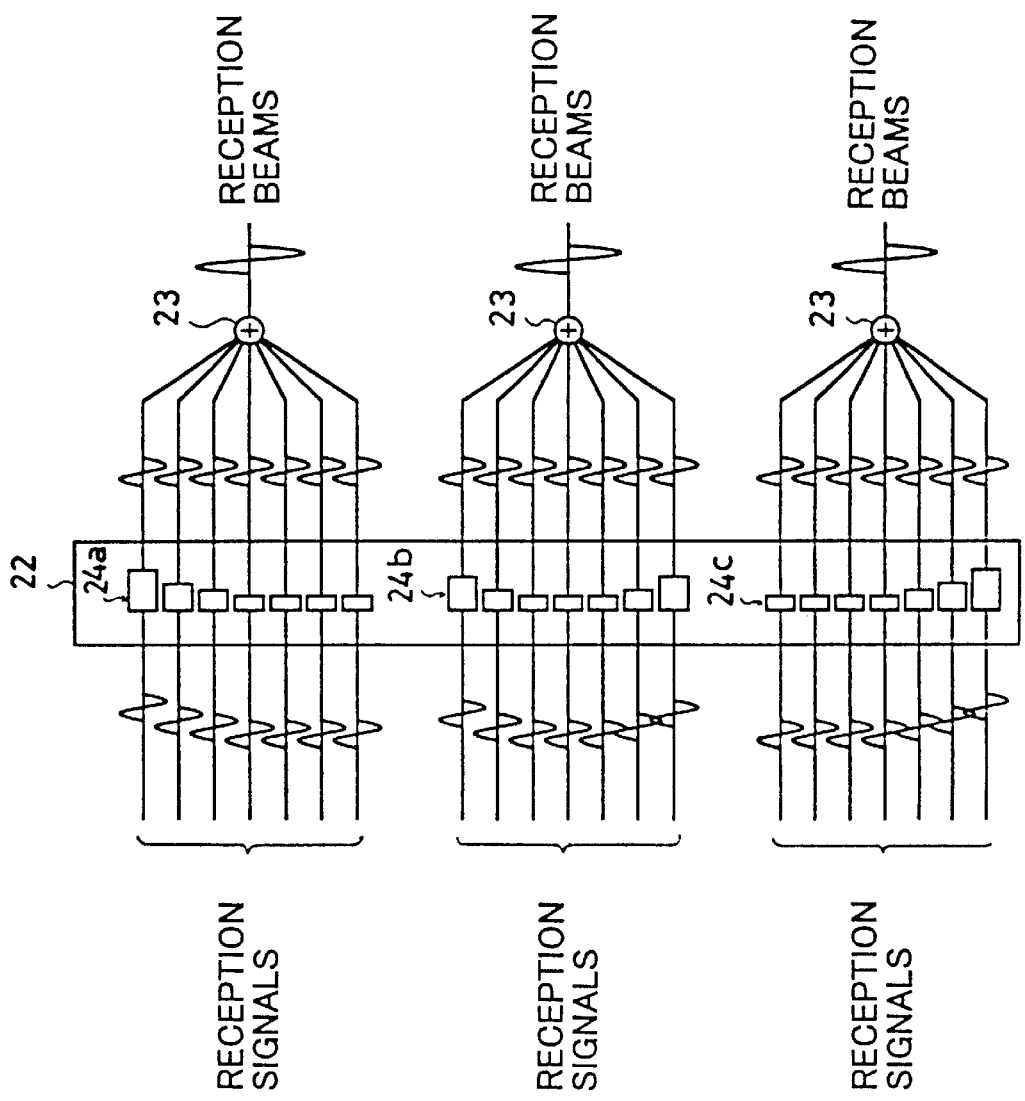
FIG. 9 is a block diagram illustrating the internal constitution of a phasing unit in a reception unit.

The probe 1 transmits and receives the ultrasonic waves into, and from, the subject, and contains a plurality of transducers that are arranged therein. The transmission unit 11 sends transmission signals to the transducers in the probe 1 to transmit ultrasonic waves, and contains, as shown in FIG. 7 or 8, a basic clock generator 18, a transmission signal timing unit 19, a transmission signal generator 20 and an amplifier 21. The reception unit 12 amplifies the reflected echo signals from the probe 1, executes the A/D conversion on the signals, executes the phasing and addition, and further executes the filtering, detection and LOG compression processings. As shown in FIG. 9, the reception unit 12 includes a phasing unit that comprises a signal delay unit 22 and adder units 23.

The signal processing unit 13 processes the reception signals from the reception unit 12, and executes filtering processings such as median, FFT and smoothing. The image storage unit 14 converts the reception signals after processed through the signal processing unit 13 into image data, executes the image processing and stores the image data in a memory for storing image, such as RAM or the like. The display unit 15 displays the image data from the image storage unit 14, and includes an image encoder and a CRT or the like.

The control unit 16 controls the operations of the above-mentioned constituent elements and comprises, for example, a CPU (central processing unit). The input device inputs operation instructions to the control unit 16, and includes buttons, switches, a track ball, a mouse, a touch panel and the like for inputting various parameters for operating and controlling the apparatus.

Here, according to the present invention, the ultrasonic probe 1 shown in FIG. 1 or 2 is used as the above-mentioned probe 1, transmission signals which are in phase are sent from the transmission unit 11 to a number of the transducers 2, 2, - - - constituting the probe I to generate a sound field equivalent to the one generated by a point source of sound without directivity and, upon receiving the reception signals from the probe 1, the reception unit 12 simultaneously generates a plurality of reception beams.

FIG. 7 is a block diagram illustrating the internal constitution of the transmission unit 11. The basic clock generator 18 generates sampling clocks for forming transmission signals for the probe 1, and is constituted by, for example, a quartz oscillator, a counter, a frequency divider, etc. The transmission signal timing unit 19 receives output signals from the basic clock generator 18 and generates timings for forming transmission signals for the probe 1, and is constituted by, for example, a storage device such as ROM or RAM, a counter, a frequency divider and the like. The transmission signal generator 20 receives output signals from the transmission signal timing unit 19 and generates transmission signals for the probe 1, and is constituted by, for example, a storage device such as ROM or RAM, a D/A converter, an operational amplifier, an FET (field-effect transistor) and the like. Furthermore, the operational amplifier 21 receives output signals from the transmission signal generator 20, amplifies them, and sends transmission signals to the probe 1, and is constituted by, for example, a transistor, an FET, an operational amplifier, a buffer memory and the like.

In this state, the transmission unit of the ultrasonic wave diagnostic apparatus using the conventional ultrasonic probe generates transmission signal timings of a number equal to the number of the transducers that transmit ultrasonic waves in order to generate a plurality of transmission signals and to amplify them. According to the present invention, however, when a plurality of amplifiers 21 are used like in the prior art, the transmission signal timings which are in phase may be supplied to the amplifiers 21 corresponding to the number N of the transducers of the probe 1. Since the transmission signal timings are in phase as described above, the amplifier 21 may be used in a number of only one as shown in FIG. 8 provided it is capable of driving the transducers. Thus, the amplifiers 21 may be employed in a minimum number depending upon their driving ability. Upon transmitting the transmission signals which are in phase generated by the transmission unit 11 shown in FIG. 7 or 8 to the probe 1 constituted as shown in FIG. 1 or 2, the sound pressure of ultrasonic waves transmitted from the probe 1 propagates uniformly in all directions, establishing a transmission from a point source of sound.

FIG. 9 is a block diagram illustrating a phasing unit in the reception unit 12. The signal delay unit 22 works to delay the plurality of reception signals received by the plurality of transducers in the probe 1 to bring them in phase, and is constituted by delay elements such as LC delay lines or RC delay lines, or by a memory such as RAM in a digital delay circuit, or a selector. The adder unit 23 adds the reception signals from the signal delay unit 22 and is constituted by an operational amplifier, a transistor, a DSP or a digital adder. FIG. 9 illustrates a case where three ultrasonic reception beams are formed. The signal delay unit 22 is provided with three delay element groups (24a, 24b, 24c) each constituted by a plurality of delay elements. The delay amount is controlled for every direction of reception signal to control the direction of the reception beam. The reception signals phased by the delay element groups 24a, 24b and 24c are added by the three adder units 23 thereby to form ultrasonic reception beams in three directions. By increasing the number of the delay element groups 24a to 24c and the adder units 23, it is allowed to increase the number of the ultrasonic reception beams and to enhance the frame rate and resolution of the ultrasonic image.

In this embodiment, when the ultrasonic reception beams are simultaneously scanned in the two-dimensional direction, an ultrasonic three-dimensional image can be obtained. Or, when the ultrasonic reception beams are scanned in the one-dimensional direction and are squeezed in a direction of 90 degrees with respect to the scanning direction, an ultrasonic tomographic image having a sharp slicing thickness in the direction of the short axis can be obtained. Or, when the ultrasonic reception beams are simultaneously scanned in the one-dimensional direction but are not squeezed in the direction of 90 degrees with respect to the scanning direction, an ultrasonic transmission tomographic image in the direction of the short axis can be obtained.

Figure 10:
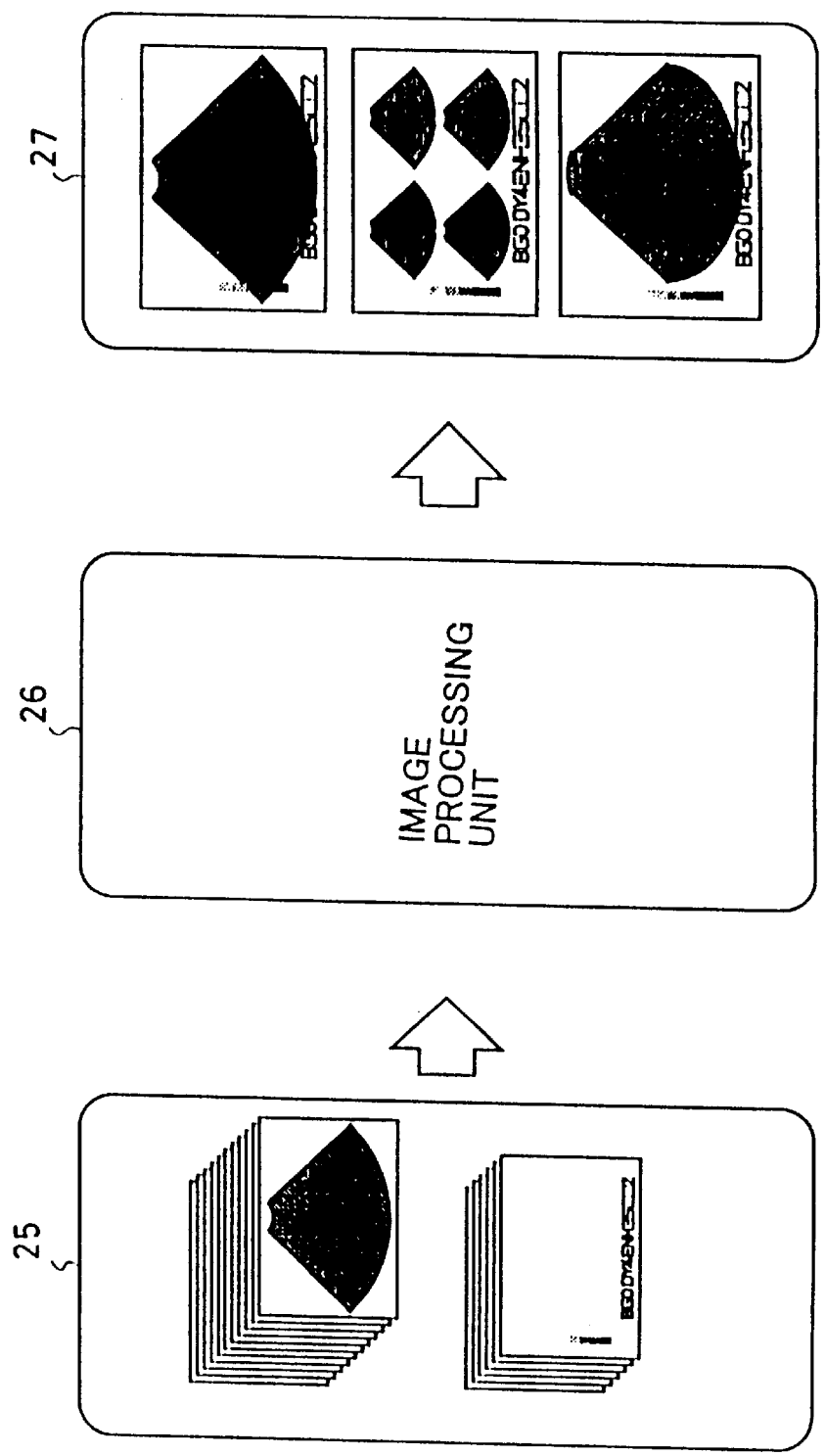
FIG. 10 is a diagram illustrating the internal constitution of an image storage unit.

FIG. 10 is a diagram illustrating the internal constitution of the image storage unit 14 which has a frame memory for storing image data for simultaneously displaying at least two or more two-dimensional tomographic images or for storing image data for displaying a three-dimensional image. If concretely described, the image storage unit 14 includes a pre-memory 25, an image processing unit 26 and a post-memory 27. The pre-memory 25 stores the reception signal data for forming diagnostic image data, diagnostic parameters such as set conditions, comments and scales, and character data such as body mark, etc., and is constituted by a storage medium such as ROM, RAM, hard disk or the like. The image processing unit 26 executes the image processings, such as interframe processing, filter processing, coordinate conversion processing, expansion and contraction, for every data read from the pre-memory 25 depending upon the systems such as two-dimensional display, three-dimensional display and split display, and is constituted by a DSP, a digital filter, a multiplier, a subtractor, an adder and a divider. The post-memory 27 stores the image data processed through the image processing unit 26 and outputs the image data to the display unit 15 in a succeeding stage, and is constituted by a storage medium such as ROM, RAM, hard disk or the like.

As described above, in the phasing unit in the reception unit 12 shown in FIG. 9 and the image storage unit 14 shown in FIG. 10, the ultrasonic reception beams are scanned at least simultaneously in the two-dimensional direction or in the three-dimensional direction. Furthermore, provision is made of the frame memory for storing image data for simultaneously displaying at least two or more two-dimensional tomographic images. It is thus made possible to display a plurality of tomographic images. In the reception unit 12 and the image storage unit 14, the ultrasonic reception beams are simultaneously scanned in the three-dimensional direction and are executed the image processing for displaying a three dimensional image, thus a three-dimensional image, such as cinematographic image, perspective image, bird's eye image, etc. can be displayed. Upon effecting the image processing for displaying a two-dimensional image from the three-dimensional image data, furthermore, it is allowed to display an ultrasonic tomographic image such as B-image or C-image, as well as a two-dimensional image such as cinematographic image or perspective image.

INDUSTRIAL APPLICABILITY

According to the present invention as described above, the transducers in the ultrasonic probe are formed in the shape of a predetermined small block and are arranged in many number in a spherical shape on the front surface of the backing member formed in a spherical surface protruding in a semicircular manner. By applying the transmission signals which are in phase to the above-mentioned number of the transducers to drive them, the sound pressure of the transmitted ultrasonic waves uniformly propagate in all directions, establishing a transmission from a point source of sound.

When the transducers of the ultrasonic probe are formed in the shape of a circular plate or a polygonal plate, and when those of the form of a circular plate only, those of the shape of a polygonal plate only, or those of the shape of the circular plate and those of the shape of the polygonal plate in combination, are arranged in a spherical shape, it is allowed to improve the directivity of the ultrasonic transmission beam by decreasing the grating lobes at the time of transmitting ultrasonic waves. Therefore, a difference in the sensitivity does not occur so much despite the number of the ultrasonic beams is increased, and no limitation is imposed on the number of the ultrasonic reception beams and it is allowed to enhance the frame rate of the obtained ultrasonic image.

Moreover, the ultrasonic diagnostic apparatus according to the invention related to the ultrasonic probe uses an ultrasonic probe shown in FIG. 1 or 2 as the probe, and sends the transmission signals which are in phase from the transmission unit to the number of the transducers constituting the probe to generate a sound field equivalent to the one generated by a point source of sound without directivity. Upon receiving reception signals from the probe, the reception unit simultaneously generates a plurality of reception beams. Therefore, the sound pressure of the transmitted ultrasonic waves uniformly propagate in all directions, establishing a transmission from a point source of sound. Besides, a difference in the sensitivity does not occur so much despite the number of the ultrasonic beams is increased, and no limitation is imposed on the number of the ultrasonic reception beams and it is allowed to enhance the frame rate of the obtained ultrasonic image.

Furthermore, when the image storage unit in the ultrasonic diagnostic apparatus has a frame memory for storing image data for simultaneously displaying at least two or more two-dimensional tomographic images or for storing image data for displaying a three-dimensional image, it is allowed to display a plurality of tomographic images. Upon executing the image processing for displaying a three-dimensional image by simultaneously scanning the ultrasonic reception beams in the three-dimensional direction, furthermore, it is allowed to display a three-dimensional image such as cinematographic image, perspective image, bird's eye image, etc. Upon effecting the image processing for displaying a two-dimensional image from the three-dimensional image data, furthermore, it is allowed to display an ultrasonic tomographic image such as B-image or C-image, as well as a two-dimensional image such as cinematographic image or perspective image.

What is claimed is:

1. An ultrasonic probe comprising a plurality of transducers for transmitting ultrasonic waves and for receiving the reflected echoes thereof, and having a backing member formed on the back surfaces of said transducers as well as an acoustic matching layer and an acoustic lens formed on the front surfaces of said transducers, wherein said transducers are arranged in a spherical shape.

2. An ultrasonic probe according to claim 1, wherein said transducers form a plurality of reception beams.

3. An ultrasonic probe comprising a plurality of transducers for transmitting ultrasonic waves and for receiving the reflected echoes thereof, and having a backing member formed on the back surfaces of said transducers as well as an acoustic matching layer and an acoustic lens formed on the front surfaces of said transducers, wherein said transducers are formed in the shape of a predetermined small block, and the number of the transducers in the form of a small block are arranged in a spherical shape on the front surface of a backing member formed in the shape of a spherical surface protruding in a semispherical manner.

4. An ultrasonic probe according to claim 2, wherein each of said transducers is formed in the shape of a circular plate or a polygonal plate, and the transducers of the shape of the circular plate only or the transducers of the shape of the polygonal plate only, or the transducers of the shape of the circular plate and the transducers of the shape of the polygonal plate in combination, are arranged in a spherical shape.

5. An ultrasonic diagnostic apparatus comprising a probe having a plurality of transducers that are arranged to transmit and receive ultrasonic waves into, and from, a subject, a transmission unit for transmitting transmission signals to the transducers in the probe to transmit ultrasonic waves, a reception unit for amplifying, phasing and adding reflected echo signals from said probe, a signal processing unit for processing reception signals from the reception unit, an image storage unit for storing image data by converting the reception signals after processed into image data and effecting an image processing, a display unit for displaying the image data from the image storage unit, a control unit for controlling the operations of said constituent elements, and an input means for inputting operation instructions to said control unit, wherein an ultrasonic probe of any one of claims 1 to 3 is used as said probe, transmission signals which are in phase are sent from said transmission unit to the number of the transducers constituting the probe to generate a sound field equivalent to the one generated by a point source of sound without directivity, and said reception unit simultaneously generates a plurality of reception beams upon receiving the reception signals from said probe.

6. An ultrasonic diagnostic apparatus according to claim 4, wherein said image storage unit has a frame memory that stores image data for simultaneously displaying at least two or more two-dimensional tomographic images or image data for displaying a three-dimensional image.

7. An ultrasonic probe comprising a plurality of transducers for transmitting ultrasonic waves and for receiving the reflected echoes thereof, and having a backing member formed on the back surfaces of said transducers as well as an acoustic matching layer and an acoustic lens formed on the front surfaces of said transducers, wherein said transducers are so arranged as to generate a sound field equivalent to the one generated by a point source of sound without directivity.

8. An ultrasonic diagnostic apparatus comprising a probe having a plurality of transducers that are arranged to transmit and receive ultrasonic waves into, and from, a subject, a transmission/reception unit for transmitting ultrasonic signals to said probe and for receiving ultrasonic signals from said probe, and an image display unit for displaying received ultrasonic signals as an image, wherein said transducers are arranged in a spherical shape.

9. An ultrasonic diagnostic apparatus according to claim 8, wherein said probe is equipped with a backing member formed in a spherical surface protruding in a semispherical manner, said transducers are formed in the shape of a predetermined small block and are arranged on the front surface of said backing member.

10. An ultrasonic diagnostic apparatus according to claim 9, wherein each of said transducers is formed in the shape of a circular plate.

11. An ultrasonic diagnostic apparatus according to claim 9, wherein each of said transducers is formed in the shape of a polygonal plate.

12. An ultrasonic diagnostic apparatus according to claim 9, wherein each of said transducers is formed in the shape of a circular plate and a polygonal plate in combination.

13. An ultrasonic diagnostic apparatus according to claim 8, wherein said transmission/reception unit simultaneously generated a plurality of reception beams upon receiving reception signals from said probe.

14. An ultrasonic diagnostic apparatus comprising a probe having a plurality of transducers that are arranged to transmit and receive ultrasonic waves into, and from, a subject, a transmission/reception unit for transmitting ultrasonic signals to said probe and for receiving ultrasonic signals from said probe, and an image display unit for displaying received ultrasonic signals as an image, wherein said transducers are so arranged as to generate a sound field equivalent to the one generated by a point source of sound without directivity.

* * * * *

UNITED STATES PATENT AND TRADEMARK OFFICE
CERTIFICATE OF CORRECTION

PATENT NO.   : 6,299,580 B1                                Page 1 of 1
DATED        : October 9, 2001
INVENTOR(S)  : Asafusa It is certified that error appears in the above-identified patent and that said Letters Patent is hereby corrected as shown below:

<u>Title page,</u>
Insert item -- [22] PCT Filed: Nov. 19, 1997 --

Signed and Sealed this

Twenty-third Day of April, 2002

Attest:

JAMES E. ROGAN
*Attesting Officer*      *Director of the United States Patent and Trademark Office*